US011319566B2

(12) United States Patent
Breit et al.

(10) Patent No.: US 11,319,566 B2
(45) Date of Patent: May 3, 2022

(54) PROCESS FOR MAKING PULLULAN

(71) Applicant: Capsugel Belgium NV, Bornem (BE)

(72) Inventors: Jeffrey F. Breit, Bend, OR (US);
Brandon J. Downey, Bend, OR (US);
Justin Beller, Bend, OR (US)

(73) Assignee: Capsugel Belgium NV, Bornem (BE)

( * ) Notice: Subject to any disclaimer, the term of this patent is extended or adjusted under 35 U.S.C. 154(b) by 102 days.

(21) Appl. No.: 16/604,550

(22) PCT Filed: Apr. 9, 2018

(86) PCT No.: PCT/IB2018/000457
§ 371 (c)(1),
(2) Date: Oct. 10, 2019

(87) PCT Pub. No.: WO2018/189587
PCT Pub. Date: Oct. 18, 2018

(65) Prior Publication Data
US 2020/0291439 A1 Sep. 17, 2020

Related U.S. Application Data

(60) Provisional application No. 62/485,855, filed on Apr. 14, 2017.

(51) Int. Cl.
*C12P 19/10* (2006.01)
*C08B 37/00* (2006.01)
(52) U.S. Cl.
CPC .......... *C12P 19/10* (2013.01); *C08B 37/0018* (2013.01)
(58) Field of Classification Search
CPC .......................... C12P 19/10; C08B 37/0018
See application file for complete search history.

(56) References Cited

U.S. PATENT DOCUMENTS

| 3,654,088 | A | 4/1972 | Coker et al. |
| 3,779,972 | A | 12/1973 | Bolles |
| 3,784,390 | A | 1/1974 | Hijiya |
| 3,827,937 | A | 8/1974 | Kato et al. |
| 3,870,537 | A | 3/1975 | Hijiya et al. |
| 3,871,892 | A | 3/1975 | Hijiya et al. |
| 3,872,228 | A | 3/1975 | Hijiya et al. |
| 3,873,333 | A | 3/1975 | Hijiya et al. |
| 3,875,308 | A | 4/1975 | Kato et al. |
| 3,888,809 | A | 6/1975 | Nakashio et al. |
| 3,912,591 | A | 10/1975 | Kato et al. |
| 3,931,146 | A | 1/1976 | Kato et al. |
| 3,932,192 | A | 1/1976 | Nakashio et al. |
| 3,936,347 | A | 2/1976 | Nomura |
| 3,954,724 | A | 5/1976 | Nakashio et al. |
| 3,959,009 | A | 5/1976 | Kato et al. |
| 3,960,685 | A | 6/1976 | Sano et al. |
| 3,962,155 | A | 6/1976 | Usamoto et al. |
| 3,972,997 | A | 8/1976 | Nakashio et al. |
| 3,976,605 | A | 8/1976 | Matsunaga et al. |
| 3,976,819 | A | 8/1976 | Mori et al. |
| 3,992,496 | A | 11/1976 | Matsunaga et al. |
| 3,993,840 | A | 11/1976 | Tsuji et al. |
| 3,997,703 | A | 12/1976 | Nakashio et al. |
| 4,004,977 | A | 1/1977 | Kato et al. |
| 4,018,233 | A | 4/1977 | Miyake |
| 4,029,616 | A | 6/1977 | Nakashio et al. |
| 4,029,886 | A | 6/1977 | Nakashio et al. |
| 4,032,403 | A | 6/1977 | Sakai et al. |
| 4,045,204 | A | 8/1977 | Matsunaga et al. |
| 4,045,388 | A | 8/1977 | Matsunaga et al. |
| 4,067,141 | A | 1/1978 | Matsunaga et al. |
| 4,152,170 | A | 5/1979 | Nagase et al. |
| 4,167,623 | A | 9/1979 | Fujita et al. |
| 4,174,440 | A | 11/1979 | Fujita et al. |
| 4,186,024 | A | 1/1980 | Fujimoto et al. |
| 4,205,218 | A | 5/1980 | Fukami et al. |
| 4,247,642 | A | 1/1981 | Hirohara et al. |
| 4,306,059 | A | 12/1981 | Yokobayashi et al. |
| 4,338,398 | A | 7/1982 | Yoneyama |
| 4,370,472 | A | 1/1983 | Igarashi et al. |
| 4,372,883 | A | 2/1983 | Matuhashi et al. |
| 4,474,756 | A | 10/1984 | Mitsuhashi et al. |
| 4,562,020 | A | 12/1985 | Hijiya et al. |
| 4,579,259 | A | 4/1986 | Hirao et al. |
| 4,610,891 | A | 9/1986 | Miyamoto et al. |
| 4,618,664 | A | 10/1986 | Ohnishi |
| 4,628,028 | A | 12/1986 | Katkocin et al. |
| 4,650,757 | A | 3/1987 | David et al. |
| 4,659,569 | A | 4/1987 | Mitsuhashi et al. |
| 4,683,298 | A | 7/1987 | Yalpani |
| 4,745,042 | A | 5/1988 | Sasago et al. |
| 4,758,660 | A | 7/1988 | Takeuchi et al. |
| 4,777,065 | A | 10/1988 | Hirao et al. |
| 4,816,445 | A | 3/1989 | Mitsuhashi et al. |

(Continued)

FOREIGN PATENT DOCUMENTS

| AU | 2018251256 | 11/2019 |
| AU | 2018253392 | 11/2019 |

(Continued)

OTHER PUBLICATIONS

Bouvens, H.O. et al., "Polysaccharides elaborated by Pullularia pullulans; Part I. The neutral glucan synthesized from sucrose solutions," *Acta Chemica Scandinavica*, 16(3):615-622 (1962).
International Search Report and Written Opinion for PCT/IB2018/000457 (dated Sep. 10, 2018).
Cade et al., "Liquid Filling in Hard Gelatin Capsules—Preliminary Steps," *Bulletin Technique Gattefosse*, 89:15-19 (1996).
European Patent Office Communication dated May 2, 2014, from EPC Patent Application No. 12705407.0 (6 pages).
International Search Report for PCT/IB2012/000176 (dated Aug. 7, 2012).
International Search Report and Written Opinion for PCT/IB2018/000448 (dated Jul. 17, 2018).
Madi, N. et al., "Effect of exogenous calcium on morphological development and biopolymer synthesis in the fungus *Aureobasidium pullulans*," *Enzyme and Microbial Technology*, 21(2):102-107 (Aug. 1997).

(Continued)

*Primary Examiner* — Leigh C Maier
(74) *Attorney, Agent, or Firm* — Klarquist Sparkman, LLP

(57) ABSTRACT

The instant disclosure provides a process for making pullulan.

20 Claims, 2 Drawing Sheets

(56) References Cited

U.S. PATENT DOCUMENTS

| | | | |
|---|---|---|---|
| 4,824,938 A | 4/1989 | Koyama et al. |
| 4,889,728 A | 12/1989 | Maeda et al. |
| 4,927,636 A | 5/1990 | Hijiya et al. |
| 4,962,026 A | 10/1990 | Keng |
| 4,965,347 A | 10/1990 | Misaki et al. |
| 5,019,514 A | 5/1991 | Bock et al. |
| 5,073,628 A | 12/1991 | Matsuhashi et al. |
| 5,077,336 A | 12/1991 | Nakashita et al. |
| 5,082,803 A | 1/1992 | Sumita |
| 5,100,877 A | 3/1992 | Mori et al. |
| 5,143,646 A | 9/1992 | Nochumson et al. |
| 5,147,795 A | 9/1992 | Ara et al. |
| 5,147,796 A | 9/1992 | Ara et al. |
| 5,264,223 A | 11/1993 | Yamamoto et al. |
| 5,268,460 A | 12/1993 | Thorne et al. |
| 5,281,527 A | 1/1994 | Tachibana et al. |
| 5,316,691 A | 5/1994 | Sone et al. |
| 5,362,779 A | 11/1994 | Kitayama et al. |
| 5,366,879 A | 11/1994 | Kitahata et al. |
| 5,411,945 A | 5/1995 | Ozaki et al. |
| 5,518,902 A | 5/1996 | Ozaki et al. |
| 5,552,166 A | 9/1996 | Harada et al. |
| 5,583,039 A | 12/1996 | Park et al. |
| 5,583,244 A | 12/1996 | Uchida et al. |
| 5,631,221 A | 5/1997 | Kohno et al. |
| 5,709,801 A | 1/1998 | Murofushi et al. |
| 5,756,123 A | 5/1998 | Yamamoto et al. |
| 5,837,673 A | 11/1998 | Tsujihara et al. |
| 5,871,088 A | 2/1999 | Tanabe |
| 5,874,401 A | 2/1999 | Sanou et al. |
| 6,242,224 B1 | 6/2001 | Nakano et al. |
| 6,368,635 B1 | 4/2002 | Akiyama et al. |
| 6,387,666 B1 | 5/2002 | Thorne et al. |
| 6,410,050 B1 | 6/2002 | Yang |
| 6,449,925 B1 | 9/2002 | Otsu et al. |
| 6,596,298 B2 | 7/2003 | Leung et al. |
| 6,610,810 B2 | 8/2003 | Phillips et al. |
| 6,887,307 B1 | 5/2005 | Scott et al. |
| 6,916,796 B2 | 7/2005 | Wolf |
| 6,972,189 B2 | 12/2005 | Han et al. |
| 7,098,013 B2 | 8/2006 | Kubota et al. |
| 7,101,533 B2 | 9/2006 | Matsuo et al. |
| 7,179,891 B2 | 2/2007 | Mayumi et al. |
| 7,186,824 B2 | 3/2007 | Aga et al. |
| 7,259,197 B2 | 8/2007 | Mitsui et al. |
| 7,237,718 B2 | 9/2007 | Scott et al. |
| 7,265,168 B2 | 9/2007 | Mitsui et al. |
| 7,265,191 B2 | 9/2007 | Kinoshita et al. |
| 7,267,718 B2 | 9/2007 | Scott et al. |
| 7,396,543 B2 | 7/2008 | Matsunaga et al. |
| 7,414,038 B2 | 8/2008 | Kinugasa et al. |
| 7,417,135 B2 | 8/2008 | Bardowski et al. |
| 7,445,921 B2 | 11/2008 | Oura et al. |
| 7,638,241 B2 | 12/2009 | Lee et al. |
| 7,749,538 B2 | 7/2010 | Sugimoto et al. |
| 7,815,935 B2 | 10/2010 | Li et al. |
| 7,815,952 B2 | 10/2010 | Inoue et al. |
| 7,856,989 B2 | 12/2010 | Karles et al. |
| 8,017,143 B2 | 9/2011 | Shin et al. |
| 8,105,625 B2 | 1/2012 | Rajewski et al. |
| 8,168,778 B2 | 5/2012 | Nishimoto et al. |
| 8,192,761 B2 | 6/2012 | Ochiai et al. |
| 8,324,375 B2 | 12/2012 | Watanabe et al. |
| 8,361,386 B2 | 1/2013 | Davis et al. |
| 8,536,111 B2 | 9/2013 | Watanabe et al. |
| 8,632,652 B2 | 1/2014 | Lee et al. |
| 8,791,232 B2 | 7/2014 | Dekx et al. |
| 8,821,934 B2 | 9/2014 | Sugimoto et al. |
| 8,900,629 B2 | 12/2014 | Rajewski et al. |
| 8,951,996 B2 | 2/2015 | Giliyar et al. |
| 8,986,735 B2 | 3/2015 | Schobel et al. |
| 9,073,294 B2 | 7/2015 | Kumar et al. |
| 2002/0009522 A1 | 1/2002 | Hirai et al. |
| 2002/0131990 A1 | 9/2002 | Barkalow et al. |
| 2003/0017209 A1 | 1/2003 | Parikh et al. |
| 2003/0054499 A1 | 3/2003 | Han et al. |
| 2003/0059479 A1 | 3/2003 | Miyake |
| 2003/0087002 A1 | 5/2003 | Fouache et al. |
| 2003/0108593 A1 | 6/2003 | Oku et al. |
| 2003/0134409 A1 | 7/2003 | Mallouk et al. |
| 2004/0013723 A1 | 1/2004 | Parikh et al. |
| 2004/0126330 A1 | 7/2004 | Awamura et al. |
| 2004/0131661 A1 | 7/2004 | Auffret et al. |
| 2004/0236017 A1 | 11/2004 | Bruzzano et al. |
| 2005/0019448 A1 | 1/2005 | Engelhardt |
| 2005/0031853 A1 | 2/2005 | Scott et al. |
| 2005/0065030 A1 | 3/2005 | Oku et al. |
| 2005/0202083 A1 | 9/2005 | Kumar et al. |
| 2005/0249676 A1 | 11/2005 | Scott et al. |
| 2006/0011118 A1 | 1/2006 | Hayashi et al. |
| 2006/0147542 A1 | 7/2006 | Ono et al. |
| 2006/0159752 A1 | 7/2006 | Jain et al. |
| 2006/0223140 A1 | 10/2006 | Oura et al. |
| 2006/0233875 A1 | 10/2006 | Mathur et al. |
| 2006/0257482 A1 | 11/2006 | Kumar et al. |
| 2007/0042035 A1 | 2/2007 | Momoi |
| 2007/0042970 A1 | 2/2007 | Sunamoto et al. |
| 2007/0087939 A1 | 4/2007 | Cade et al. |
| 2007/0092600 A1 | 4/2007 | Miyai et al. |
| 2007/0099996 A1 | 5/2007 | Isloor |
| 2007/0218189 A1 | 9/2007 | Oku et al. |
| 2007/0219250 A1 | 9/2007 | Singh et al. |
| 2007/0258941 A1 | 11/2007 | Pfister |
| 2007/0292481 A1 | 12/2007 | Hoffman et al. |
| 2008/0008750 A1 | 1/2008 | Tochio et al. |
| 2008/0038432 A1 | 2/2008 | Hoffman et al. |
| 2008/0223395 A1 | 9/2008 | Maillefer et al. |
| 2008/0248102 A1 | 10/2008 | Rajewski et al. |
| 2008/0274187 A1 | 11/2008 | Cao |
| 2009/0048188 A1 | 2/2009 | Matsuo et al. |
| 2009/0110728 A1 | 4/2009 | Rastogi et al. |
| 2009/0274636 A1 | 11/2009 | Shinohara et al. |
| 2009/0291138 A1 | 11/2009 | Watanabe et al. |
| 2010/0003590 A1 | 1/2010 | Park et al. |
| 2010/0093875 A1 | 4/2010 | Matsui et al. |
| 2010/0166690 A1 | 7/2010 | Masachika |
| 2011/0015309 A1 | 1/2011 | Brocket et al. |
| 2011/0020757 A1 | 1/2011 | Kawauchi et al. |
| 2011/0086070 A1 | 4/2011 | Talwar et al. |
| 2011/0091814 A1 | 4/2011 | Endo |
| 2011/0139164 A1 | 6/2011 | Mua et al. |
| 2011/0177137 A1 | 7/2011 | Chauhan et al. |
| 2011/0177297 A1 | 7/2011 | Jung et al. |
| 2011/0206729 A1 | 8/2011 | Akiyoshi et al. |
| 2011/0207686 A1 | 8/2011 | Lecommandoux et al. |
| 2011/0236935 A1 | 9/2011 | Mikkelsen et al. |
| 2011/0244047 A1 | 10/2011 | Asari et al. |
| 2011/0268797 A1 | 11/2011 | Cifter et al. |
| 2011/0292566 A1 | 12/2011 | Tan et al. |
| 2012/0037039 A1 | 2/2012 | Nieto |
| 2013/0005831 A1 | 1/2013 | Rajewski et al. |
| 2013/0160779 A1 | 6/2013 | Chida et al. |
| 2013/0195941 A1 | 8/2013 | Shibuya et al. |
| 2013/0244082 A1 | 9/2013 | Lee et al. |
| 2013/0287842 A1 | 10/2013 | Cade et al. |
| 2013/0288932 A1 | 10/2013 | Mackenzie et al. |
| 2013/0323307 A1 | 12/2013 | Jeon et al. |
| 2013/0344147 A1 | 12/2013 | Kainose et al. |
| 2014/0010882 A1 | 1/2014 | Matsuda et al. |
| 2014/0170213 A1 | 6/2014 | Kim et al. |
| 2014/0178555 A1 | 6/2014 | Fujimoto et al. |
| 2014/0187538 A1 | 7/2014 | Bogo et al. |
| 2015/0111862 A1 | 4/2015 | Podolski |
| 2015/0112250 A1 | 4/2015 | Kwon |
| 2015/0209275 A1 | 7/2015 | Choonara et al. |
| 2015/0274605 A1 | 10/2015 | Waldron et al. |
| 2016/0038729 A1 | 2/2016 | Kato |
| 2018/0256506 A1 | 9/2018 | Cade et al. |

(56) References Cited

U.S. PATENT DOCUMENTS

| | | | |
|---|---|---|---|
| 2019/0046454 | A1 | 2/2019 | Cade et al. |
| 2020/0289422 | A1 | 9/2020 | Takubo et al. |

FOREIGN PATENT DOCUMENTS

| | | |
|---|---|---|
| BR | 112019021396 | 4/2020 |
| BR | 112019021391 | 5/2020 |
| CA | 1037887 | 9/1978 |
| CA | 2520986 | 4/2000 |
| CA | 3059529 | 10/2018 |
| CA | 3059527 | 10/2019 |
| CN | 1216780 | 5/1999 |
| CN | 1216781 | 5/1999 |
| CN | 1106448 | 4/2003 |
| CN | 1449741 | 10/2003 |
| CN | 1584596 | 2/2005 |
| CN | 1602716 | 4/2005 |
| CN | 1609188 | 4/2005 |
| CN | 1644675 | 7/2005 |
| CN | 1289532 | 8/2005 |
| CN | 1313498 | 8/2005 |
| CN | 1651467 | 8/2005 |
| CN | 1651468 | 8/2005 |
| CN | 1654482 | 8/2005 |
| CN | 1680571 | 10/2005 |
| CN | 1696302 | 11/2005 |
| CN | 1723904 | 1/2006 |
| CN | 1768860 | 5/2006 |
| CN | 1264976 | 7/2006 |
| CN | 1948347 | 4/2007 |
| CN | 1315873 | 5/2007 |
| CN | 101036788 | 9/2007 |
| CN | 101069677 | 11/2007 |
| CN | 101088879 | 12/2007 |
| CN | 101100687 | 1/2008 |
| CN | 101229379 | 7/2008 |
| CN | 101254309 | 9/2008 |
| CN | 101283774 | 10/2008 |
| CN | 101416930 | 4/2009 |
| CN | 101555507 | 10/2009 |
| CN | 101560528 | 10/2009 |
| CN | 100571781 | 12/2009 |
| CN | 101653171 | 2/2010 |
| CN | 101096236 | 5/2010 |
| CN | 101731410 | 6/2010 |
| CN | 101755991 | 6/2010 |
| CN | 101760456 | 6/2010 |
| CN | 101831000 | 9/2010 |
| CN | 101836678 | 9/2010 |
| CN | 101839849 | 9/2010 |
| CN | 101942493 | 1/2011 |
| CN | 101988036 | 3/2011 |
| CN | 101279096 | 4/2011 |
| CN | 102010526 | 4/2011 |
| CN | 102027999 | 4/2011 |
| CN | 101215592 | 8/2011 |
| CN | 102258484 | 11/2011 |
| CN | 101974543 | 5/2012 |
| CN | 102492630 | 6/2012 |
| CN | 101579326 | 7/2012 |
| CN | 102552721 | 7/2012 |
| CN | 102626279 | 8/2012 |
| CN | 102670563 | 9/2012 |
| CN | 102766219 | 11/2012 |
| CN | 102010513 | 1/2013 |
| CN | 102875742 | 1/2013 |
| CN | 101669670 | 2/2013 |
| CN | 102432921 | 4/2013 |
| CN | 103015175 | 4/2013 |
| CN | 103030978 | 4/2013 |
| CN | 102499451 | 5/2013 |
| CN | 101487034 | 6/2013 |
| CN | 102499910 | 6/2013 |
| CN | 102492740 | 8/2013 |
| CN | 103243135 | 8/2013 |
| CN | 102145173 | 10/2013 |
| CN | 102600493 | 12/2013 |
| CN | 103503983 | 12/2013 |
| CN | 102603912 | 1/2014 |
| CN | 103060204 | 2/2014 |
| CN | 103570842 | 2/2014 |
| CN | 102531773 | 3/2014 |
| CN | 103626885 | 3/2014 |
| CN | 103636743 | 3/2014 |
| CN | 103642086 | 3/2014 |
| CN | 102783713 | 4/2014 |
| CN | 103695476 | 4/2014 |
| CN | 103695500 | 4/2014 |
| CN | 103724709 | 4/2014 |
| CN | 103740785 | 4/2014 |
| CN | 103798253 | 5/2014 |
| CN | 103805650 | 5/2014 |
| CN | 103805651 | 5/2014 |
| CN | 103806275 | 5/2014 |
| CN | 103880762 | 6/2014 |
| CN | 103881927 | 6/2014 |
| CN | 103882076 | 6/2014 |
| CN | 102994395 | 7/2014 |
| CN | 103893107 | 7/2014 |
| CN | 103088085 | 8/2014 |
| CN | 103961334 | 8/2014 |
| CN | 103961335 | 8/2014 |
| CN | 103993042 | 8/2014 |
| CN | 103305569 | 9/2014 |
| CN | 104059560 | 9/2014 |
| CN | 104082851 | 10/2014 |
| CN | 103409480 | 11/2014 |
| CN | 104222265 | 12/2014 |
| CN | 103172757 | 1/2015 |
| CN | 103255067 | 1/2015 |
| CN | 103451108 | 1/2015 |
| CN | 104256251 | 1/2015 |
| CN | 103416694 | 2/2015 |
| CN | 104401075 | 3/2015 |
| CN | 104403135 | 3/2015 |
| CN | 104432492 | 3/2015 |
| CN | 104436204 | 3/2015 |
| CN | 104448019 | 3/2015 |
| CN | 104448403 | 3/2015 |
| CN | 104450827 | 3/2015 |
| CN | 104473822 | 4/2015 |
| CN | 104479038 | 4/2015 |
| CN | 104609992 | 5/2015 |
| CN | 104611783 | 5/2015 |
| CN | 104651405 | 5/2015 |
| CN | 104694404 | 6/2015 |
| CN | 104711374 | 6/2015 |
| CN | 104725652 | 6/2015 |
| CN | 103163128 | 7/2015 |
| CN | 104762753 | 7/2015 |
| CN | 104798975 | 7/2015 |
| CN | 104799145 | 7/2015 |
| CN | 104824508 | 8/2015 |
| CN | 104840447 | 8/2015 |
| CN | 104844810 | 8/2015 |
| CN | 104857560 | 8/2015 |
| CN | 104859237 | 8/2015 |
| CN | 104861178 | 8/2015 |
| CN | 104861214 | 8/2015 |
| CN | 104861246 | 8/2015 |
| CN | 102552191 | 9/2015 |
| CN | 104906622 | 9/2015 |
| CN | 104911231 | 9/2015 |
| CN | 104911232 | 9/2015 |
| CN | 104927266 | 9/2015 |
| CN | 102964849 | 10/2015 |
| CN | 103351629 | 11/2015 |
| CN | 105028864 | 11/2015 |
| CN | 105039276 | 11/2015 |
| CN | 105039281 | 11/2015 |
| CN | 105055365 | 11/2015 |
| CN | 105106181 | 12/2015 |
| CN | 105267060 | 1/2016 |
| CN | 103789363 | 2/2016 |

(56) References Cited

FOREIGN PATENT DOCUMENTS

| | | |
|---|---|---|
| CN | 110678170 | 1/2020 |
| CN | 110678555 | 1/2020 |
| CS | 200778 | 9/1980 |
| DE | 2504108 | 1/1976 |
| DE | 3147193 | 6/1983 |
| DE | 261609 | 11/1988 |
| EP | 0143603 | 6/1985 |
| EP | 0164933 | 12/1985 |
| EP | 0216221 | 4/1987 |
| EP | 0222302 | 5/1987 |
| EP | 0236124 | 9/1987 |
| EP | 0267788 | 5/1988 |
| EP | 0289138 | 11/1988 |
| EP | 0313993 | 5/1989 |
| EP | 0319372 | 6/1989 |
| EP | 0189461 | 7/1990 |
| EP | 0379378 | 7/1990 |
| EP | 0382355 | 8/1990 |
| EP | 0402092 | 12/1990 |
| EP | 0405283 | 1/1991 |
| EP | 0418835 | 3/1991 |
| EP | 0450627 | 10/1991 |
| EP | 0450767 | 10/1991 |
| EP | 0482576 | 4/1992 |
| EP | 0514008 | 11/1992 |
| EP | 0538049 | 4/1993 |
| EP | 0559450 | 9/1993 |
| EP | 0565106 | 10/1993 |
| EP | 0586034 | 3/1994 |
| EP | 0600730 | 6/1994 |
| EP | 0661294 | 7/1995 |
| EP | 0670368 | 9/1995 |
| EP | 0757049 | 2/1997 |
| EP | 0761692 | 3/1997 |
| EP | 0812919 | 12/1997 |
| EP | 0653931 | 9/1999 |
| EP | 1072633 | 1/2001 |
| EP | 0714656 | 2/2001 |
| EP | 1106347 | 6/2001 |
| EP | 1157691 | 11/2001 |
| EP | 1166745 | 1/2002 |
| EP | 1308505 | 5/2003 |
| EP | 1335020 | 8/2003 |
| EP | 1398346 | 3/2004 |
| EP | 0784688 | 7/2004 |
| EP | 1454918 | 9/2004 |
| EP | 1454950 | 9/2004 |
| EP | 1621211 | 2/2006 |
| EP | 1698239 | 9/2006 |
| EP | 1873254 | 1/2008 |
| EP | 1117736 | 8/2008 |
| EP | 2135883 | 12/2009 |
| EP | 2151500 | 2/2010 |
| EP | 2447269 | 5/2012 |
| EP | 2583982 | 4/2013 |
| EP | 2663294 | 11/2013 |
| EP | 2683830 | 1/2014 |
| EP | 3609476 | 2/2020 |
| EP | 3610028 | 2/2020 |
| FR | 2167986 | 8/1973 |
| FR | 2259905 | 8/1975 |
| FR | 2276007 | 1/1976 |
| FR | 2362888 | 3/1978 |
| FR | 2517326 | 6/1983 |
| FR | 2528060 | 12/1983 |
| FR | 2817264 | 5/2002 |
| GB | 1260418 | 1/1972 |
| GB | 1443918 | 7/1976 |
| GB | 1493411 | 11/1977 |
| GB | 1496017 | 12/1977 |
| GB | 1502797 | 3/1978 |
| GB | 1559644 | 1/1980 |
| GB | 2109391 | 6/1983 |
| GB | 2173088 | 10/1986 |
| IN | 0434/DEL/2001 | 9/2008 |
| IN | 2718/BOM/2009 | 2/2012 |
| IN | 1374/DEL/2012 | 5/2012 |
| JP | S4821739 | 3/1973 |
| JP | S497492 | 1/1974 |
| JP | S4983779 | 8/1974 |
| JP | S49117688 | 11/1974 |
| JP | S5019943 | 3/1975 |
| JP | S50105887 | 8/1975 |
| JP | S50108357 | 8/1975 |
| JP | S50123931 | 9/1975 |
| JP | S50148490 | 11/1975 |
| JP | S511699 | 1/1976 |
| JP | S517189 | 1/1976 |
| JP | S5144163 | 4/1976 |
| JP | S5152484 | 5/1976 |
| JP | S52109535 | 9/1977 |
| JP | S52130993 | 11/1977 |
| JP | S5326867 | 3/1978 |
| JP | S5379972 | 7/1978 |
| JP | S5437888 | 3/1979 |
| JP | S5437889 | 3/1979 |
| JP | S55118369 | 9/1980 |
| JP | S56147801 | 11/1981 |
| JP | S5894364 | 6/1983 |
| JP | S59172566 | 9/1984 |
| JP | S61171405 | 8/1986 |
| JP | S61263915 | 11/1986 |
| JP | S6262521 | 3/1987 |
| JP | S63283593 | 11/1988 |
| JP | H01197432 | 8/1989 |
| JP | H0321602 | 1/1991 |
| JP | H0515368 | 1/1993 |
| JP | H0525201 | 2/1993 |
| JP | H0565222 | 3/1993 |
| JP | H0594667 | 4/1993 |
| JP | H05111364 | 5/1993 |
| JP | H05148303 | 6/1993 |
| JP | H05328988 | 12/1993 |
| JP | H0665302 | 3/1994 |
| JP | H06157313 | 6/1994 |
| JP | H0710901 | 1/1995 |
| JP | H0725891 | 1/1995 |
| JP | H0725903 | 1/1995 |
| JP | H0759585 | 3/1995 |
| JP | H0790250 | 4/1995 |
| JP | H0847378 | 2/1996 |
| JP | H08175983 | 7/1996 |
| JP | H08205865 | 8/1996 |
| JP | H093106 | 1/1997 |
| JP | H10155697 | 6/1998 |
| JP | H10215892 | 8/1998 |
| JP | H10229839 | 9/1998 |
| JP | H1139450 | 2/1999 |
| JP | H1195405 | 4/1999 |
| JP | H11240806 | 9/1999 |
| JP | 2000041583 | 2/2000 |
| JP | 2000202003 | 7/2000 |
| JP | 2000294439 | 10/2000 |
| JP | 2000327699 | 11/2000 |
| JP | 2000348958 | 12/2000 |
| JP | 2001048765 | 2/2001 |
| JP | 2001095514 | 4/2001 |
| JP | 2001191446 | 7/2001 |
| JP | 2001250733 | 9/2001 |
| JP | 2001316237 | 11/2001 |
| JP | 2002033231 | 1/2002 |
| JP | 2002045118 | 2/2002 |
| JP | 2003134971 | 5/2003 |
| JP | 2003238151 | 8/2003 |
| JP | 2003265111 | 9/2003 |
| JP | 2003310295 | 11/2003 |
| JP | 2003313145 | 11/2003 |
| JP | 2004097233 | 4/2004 |
| JP | 2004306534 | 11/2004 |
| JP | 2005112744 | 4/2005 |
| JP | 2005137935 | 6/2005 |
| JP | 2005298644 | 10/2005 |
| JP | 2005302320 | 10/2005 |
| JP | 2005341958 | 12/2005 |

(56) References Cited

FOREIGN PATENT DOCUMENTS

| | | |
|---|---|---|
| JP | 2006026544 | 2/2006 |
| JP | 2006101714 | 4/2006 |
| JP | 2006143808 | 6/2006 |
| JP | 2006247505 | 9/2006 |
| JP | 2007006978 | 1/2007 |
| JP | 2007089569 | 4/2007 |
| JP | 2007238908 | 9/2007 |
| JP | 2007321003 | 12/2007 |
| JP | 2007536308 | 12/2007 |
| JP | 2008011807 | 1/2008 |
| JP | 2008050542 | 3/2008 |
| JP | 2008133186 | 6/2008 |
| JP | 2008162966 | 7/2008 |
| JP | 2008208092 | 9/2008 |
| JP | 2008208120 | 9/2008 |
| JP | 2008266458 | 11/2008 |
| JP | 2009039064 | 2/2009 |
| JP | 2009161522 | 7/2009 |
| JP | 2009185022 | 8/2009 |
| JP | 2009232818 | 10/2009 |
| JP | 2009233170 | 10/2009 |
| JP | 2010051327 | 3/2010 |
| JP | 2010053122 | 3/2010 |
| JP | 2010158253 | 7/2010 |
| JP | 2010523594 | 7/2010 |
| JP | 2010227042 | 10/2010 |
| JP | 2011182709 | 9/2011 |
| JP | 2012015152 | 1/2012 |
| JP | 2012016309 | 1/2012 |
| JP | 2012017326 | 1/2012 |
| JP | 2012062279 | 3/2012 |
| JP | 2012167273 | 9/2012 |
| JP | 2013000111 | 1/2013 |
| JP | 2015048316 | 3/2015 |
| JP | 2015177783 | 10/2015 |
| JP | 2020512827 | 4/2020 |
| JP | 2020516683 | 6/2020 |
| KR | 19890003762 | 4/1989 |
| KR | 19940014797 | 7/1994 |
| KR | 19970062047 | 2/1996 |
| KR | 20010083600 | 9/2001 |
| KR | 20020066298 | 8/2002 |
| KR | 100508434 | 8/2005 |
| KR | 100739022 | 7/2007 |
| KR | 20100100496 | 3/2009 |
| KR | 20090036797 | 4/2009 |
| KR | 20110037739 | 4/2011 |
| KR | 20110089044 | 8/2011 |
| KR | 20120064008 | 6/2012 |
| PL | 164352 | 7/1994 |
| RO | 90437 | 10/1986 |
| RO | 105830 | 12/1992 |
| RO | 116203 | 11/2000 |
| RO | 116212 | 11/2000 |
| RS | 20080223 | 4/2011 |
| RU | 2034923 | 5/1995 |
| SU | 1559718 | 12/1994 |
| WO | WO98/08399 | 3/1998 |
| WO | WO00/47190 | 8/2000 |
| WO | WO00/54606 | 9/2000 |
| WO | WO01/07507 | 2/2001 |
| WO | WO02/46241 | 6/2002 |
| WO | WO02/072862 | 9/2002 |
| WO | WO03/039522 | 5/2003 |
| WO | WO03/105605 | 12/2003 |
| WO | WO2004/012720 | 2/2004 |
| WO | WO2004/041926 | 5/2004 |
| WO | WO2004/056336 | 7/2004 |
| WO | WO2004/078959 | 9/2004 |
| WO | WO2004/096182 | 11/2004 |
| WO | WO2004/096283 | 11/2004 |
| WO | WO2005/006874 | 1/2005 |
| WO | WO2005/016315 | 2/2005 |
| WO | WO2005/020979 | 3/2005 |
| WO | WO2005/079751 | 9/2005 |
| WO | WO2005/082330 | 9/2005 |
| WO | WO2005/084433 | 9/2005 |
| WO | WO2005/105051 | 11/2005 |
| WO | WO2006/018814 | 2/2006 |
| WO | WO2006/033942 | 3/2006 |
| WO | WO2006/082842 | 8/2006 |
| WO | WO2007/011222 | 1/2007 |
| WO | WO2007/095977 | 8/2007 |
| WO | WO2008/047846 | 4/2008 |
| WO | WO2008/101894 | 8/2008 |
| WO | WO2008/124617 | 10/2008 |
| WO | WO2008/137832 | 11/2008 |
| WO | WO2009/050646 | 4/2009 |
| WO | WO2009/123257 | 10/2009 |
| WO | WO2009/138920 | 11/2009 |
| WO | WO2009/154320 | 12/2009 |
| WO | WO2010/139100 | 12/2010 |
| WO | WO2013/085021 | 6/2013 |
| WO | WO2013/123623 | 8/2013 |
| WO | WO2013/146669 | 10/2013 |
| WO | WO2013/162707 | 10/2013 |
| WO | WO2014/000425 | 1/2014 |
| WO | WO2014/051023 | 4/2014 |
| WO | WO2014/072716 | 5/2014 |
| WO | WO2014/209246 | 12/2014 |
| WO | WO2015/092939 | 6/2015 |
| WO | WO2015/133439 | 9/2015 |
| WO | WO2018/189584 | 10/2018 |
| WO | WO2018/189587 | 10/2018 |

OTHER PUBLICATIONS

Millender, "Capsule Shell Composition and Manufacturing," in Multiparticulate Oral Drug Delivery. Drugs and the Pharmaceutical Sciences, 65:357-383, New York, New York, USA: Marcel Dekker, Inc., 1994.

Morris, "Quantitative determination of carbohydrates with Dreywood's anthrone reagent," *Science*, 107:254-255 (Mar. 1948).

Notice of Reasons for Rejection dated May 12, 2015, from related Japanese Patent Application No. 2013-548905, with English-language translation (9 pages).

"Opinion of the Scientific Panel on Food Additives, Flavourings, Processing Aids, and Materials in Contact with Food on a Request from the Commission related to Pullulan PI-20 for use as a new food additive," *The EFSA Journal*, vol. 85, pp. 1-32, (Jul. 13, 2004).

Petition for Inter Partes Review of U.S. Pat. No. 6,887,307, filed Jul. 27, 2015.

Petition for Inter Partes Review of U.S. Pat. No. 7,267,718, filed Jul. 27, 2015.

"Pullulan," Official Monographs, USP 32-NF 27, 1330-1331, Dec. 1, 2008.

Seo, H. et al., "Production of high molecular weight pullulan by Aureobasidium pullulans HP-2001 with soybean pomace as nitrogen source," *Bioresource Technology*, 95(3):293-299 (Dec. 2004).

Tarcha, *Polymers for Controlled Drug Delivery*, CRC Press, p. 55, 1991.

Written Opinion for PCT/IB2012/000176 (dated Aug. 7, 2012).

Office Action for U.S. Appl. No. 16/604,540 (dated Sep. 23, 2020).

Office Action for European Application No. 18724311.8, dated Nov. 6, 2020.

Xiao, Hong-Su et al., "Phenotypic Plasticity in *Aureobasidium pullulans* Isolates," *International Journal of Agricultural & Biology*, 22(1):167-177 (Jan. 2019).

PROCESS FOR MAKING PULLULAN

CROSS REFERENCE TO RELATED APPLICATIONS

This application is the U.S. National Stage of International Application No. PCT/IB2018/1000457, filed Apr. 9, 2018, which was Published in English under PCT Article 21(2), which in turn claims the benefit of U.S. Provisional Application No. 62/485,855, filed Apr. 14, 2017, each of which is herein incorporated by reference in its entirety.

SUMMARY

Disclosed are processes for the production of pullulan by microorganisms in a fermentation medium containing calcium phosphate as a principal phosphate source.

Pullulan is a polymer of glucose, more particularly, a polysaccharide consisting of α-1,4-linked maltotriose units which are connected by α-1,6-linkages between the terminal glucosidic residues of the trisaccharide.

Pullulan is obtained from a strain of *Aureobasidium pullulans* extracellularly when the strain is cultured aerobically in a fermentation medium. The degrees of polymerization of the thus obtained pullulan are reported as falling in the range of a few hundreds to a several thousand kilodaltons (kDa). High product quality consistency can be obtained by controlling the fermentation process.

The films formed with pullulan have a variety of properties that make such films suitable for forming products such as capsules. Such resulting films have excellent homogeneity and transparency. In addition, such films have very low oxygen permeability. Accordingly, capsules made from pullulan are particularly useful for the filling of oxygen sensitive products such as fish and vegetable oils. Such films and resulting capsules made from pullulan also have relatively low water content, and exhibit high stability over storage, such as with respect to mechanical and dissolution properties.

The natural origin of pullulan and its superior properties as a film forming material has made pullulan a desired polymer for the manufacture of capsules having ingredients of all natural origin. This would enable capsules made with pullulan to meet the requirements for "organic" labeling. Notwithstanding the commercial need for a capsule meeting the organic labeling requirements, no satisfactory pullulan capsules have to date been developed that meet the organic labeling requirement. This is primarily due to the absence of pullulan as a raw material that has been made so as to satisfy the organic labeling requirements.

In one embodiment, a process for manufacturing pullulan is provided, comprising: a. preparing a fermentation medium comprising water, a nitrogen source, a carbon source, a phosphate source, and a magnesium source; b. inoculating said fermentation medium with a pullulan producing microorganism; c. culturing said microorganism in said fermentation medium so as to produce pullulan in said fermentation medium; wherein said phosphate source comprises calcium phosphate.

In one embodiment, the phosphate source comprises, consists essentially of or consists of calcium phosphate.

In one embodiment, the fermentation medium has an initial calcium phosphate concentration of from about 0.25 g/L to about 4 g/L.

In one embodiment, the magnesium source is magnesium chloride.

In one embodiment, the fermentation medium has an initial concentration of magnesium chloride of from 0.01 g/L to 1 g/L.

In one embodiment, the nitrogen source is yeast extract, $NH_4OH$, L-glutamine, $NaNO_3$, $NH_4Cl$, arginine, or a mixture thereof.

In one embodiment, the nitrogen source is yeast extract.

In one embodiment, the carbon source is glucose, maltose, lactose, sucrose, fruit and vegetable syrups, fruit and vegetable molasses, or a mixture thereof.

In one embodiment, the carbon source is sucrose.

In one embodiment, the microorganism is *Aureobasidium pullulans*.

In one embodiment, the microorganism is *Aureobasidium pullulans* ATCC No. 42023.

In one embodiment, the culturing of the microorganism is stopped by pasteurization.

In one embodiment, the molecular weight of the pullulan is reduced by pullulanase produced by the microorganism, and the process is free from a step of adding an acid or heat to reduce the molecular weight of the pullulan.

In one embodiment, the fermentation medium has an initial pH of from 2.5 to 8.

In one embodiment, the microorganism is cultured for at least 3 days.

In one embodiment, pullulan is produced from the foregoing processes.

In one embodiment, the pullulan has a molecular weight of from 200 to 500 kDa.

In one embodiment, the pullulan has a $Ca^{2+}$ content of at least 50 mg/kg, or at least 100 mg/kg, or at least 200 mg/kg, or at least 300 mg/kg, or even at least 500 mg/kg.

In one embodiment, the pullulan has a $Mg^{2+}$ content of at least 10 mg/kg, or 20 mg/kg, or 30 mg/kg, or at least 40 mg/kg, or even at least 50 mg/kg.

In one embodiment, the pullulan has a ratio of $(Mg^{2+}+Ca^{2+})/K^+$ that is greater than 3, or greater than 5, or greater than 10, or even greater than 15.

It is to be understood that both the foregoing general description and the following detailed description are exemplary and explanatory only and are not restrictive of the claimed subject matter.

DETAILED DESCRIPTION

Definitions

Figure 1:
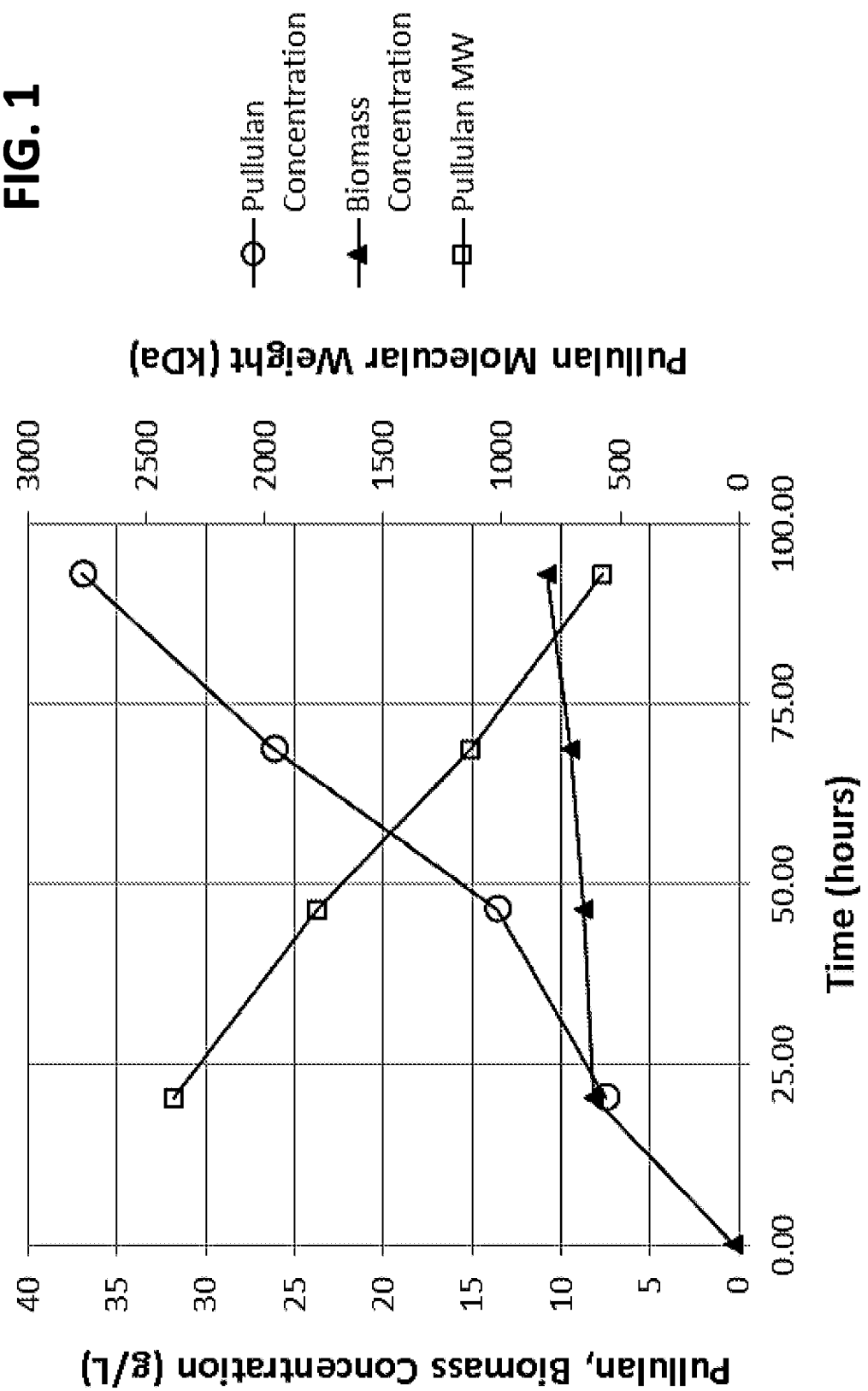
FIG. 1 is a time course plot of pullulan concentration, molecular weight, and biomass concentration measured in Example 1.

As used herein, reference to an element by the indefinite article "a" or "an" does not exclude the possibility that more than one of the element is present, unless the context clearly requires that there is one and only one of the elements. The indefinite article "a" or "an" thus usually means "at least one." The disclosure of numerical ranges should be understood as referring to each discrete point within the range, inclusive of endpoints, unless otherwise noted. The term "about" as used in the disclosure of numerical ranges indicates that deviation from the stated value is acceptable to the extent that the deviation is the result of measurement variability and/or yields a product of the same or similar properties.

As used herein, "w/w %" and "wt %" means by weight as a percentage of the total weight.

Process for Making Pullulan

A process for manufacturing pullulan comprises the steps of
 a. preparing a fermentation medium comprising water, a nitrogen source, a carbon source, a phosphate source, and a magnesium source;
 b. inoculating said fermentation medium with a pullulan producing microorganism;
 c. culturing said microorganism in said fermentation medium so as to produce pullulan in said fermentation medium.

The fermentation medium may contain any carbon source suitable for the production of pullulan. Suitable known carbon sources include saccharides such as sucrose, fructose, and glucose; modified saccharides such as isomerized sugar, and invert sugar; carbohydrates such as starch; and natural products such as tapioca and dates. In a preferred embodiment, the carbon source is certified as meeting organic labeling requirements. In one embodiment, the carbon source is sucrose. The carbon source, for example, sucrose, is initially present in the fermentation medium at a concentration of from 10 g/L to 200 g/L, more preferably from 60 g/L to 110 g/L.

The fermentation medium may contain any nitrogen source suitable for the production of pullulan. Generally, ammonium salts, nitrates, peptone and yeast extract may be used as nitrogen sources. In a preferred embodiment, the nitrogen source is certified as meeting organic labeling requirements. In one embodiment, the nitrogen source is yeast extract. The nitrogen source, for example, yeast extract, is present in the fermentation medium initially at a concentration of from 1 g/L to 6 g/L (0.08 g/L to 0.4 g/L nitrogen equivalent).

The fermentation medium also contains a phosphate source comprising calcium phosphate. In one embodiment, the phosphate source consists of calcium phosphate. Calcium phosphate is a preferred source of phosphate as it is capable of being certified as meeting organic labeling requirements. The calcium phosphate is present in the fermentation medium initially at a concentration of from 0.25 g/L to 4 g/L.

The fermentation medium also contains a magnesium source suitable for the manufacture of pullulan. In one embodiment, the magnesium source consists of magnesium chloride. Magnesium chloride is a preferred source of magnesium as it is capable of being certified as meeting organic labeling requirements. The magnesium source is present in the fermentation medium initially at a concentration of from 0.01 g/L to 1 g/L. (0.1 mM to 10.5 mM Mg or 0.002 g/L to 0.26 g/L Mg)

The fermentation medium may contain other optional materials. In one embodiment, the fermentation medium may contain ascorbic acid. The ascorbic acid may be present in an amount of from 0.2 mg/ml to 3 mg/ml of the initial fermentation medium.

Other optional materials that may be included in the fermentation medium include salts such as sodium chloride.

The pH of the fermentation medium may range from 2.5 to 8. The pH of the fermentation medium may be adjusted by addition of acids, bases, or buffers, such as sodium hydroxide, and hydrochloric acid.

The fermentation medium may be prepared in any vessel suitable for culturing microorganisms, such as shake flasks or bioreactors. The fermentation medium ingredients and water are added to the vessel and stirred or agitated to dissolve or uniformly disperse the ingredients. The fermentation medium is then sterilized, for example, by heating to a temperature of at least 60 C for at least 30 min time prior to introduction of the microorganism.

The pullulan producing microorganisms employable in the present invention include *Aureobasidium pullulans*, *Pullularia fermentans* var *fermentans* IFO 6401, *Pullularia fermentans* var *fusca* IFO 6402, *Pullularia pullulans* AHU 9553, *Pullularia pullulans* IFO 6353, and *Dematium pullulans* IFO 4464. A preferred pullulan producing microorganism is *Aureobasidium pullulans*. *Aureobasidium pullulans* may be obtained from ATCC. A preferred clone is *Aureobasidium pullulans* ATCC No. 42023.

After heat sterilizing of the fermentation medium and pH adjustment, the microorganism is cultured in the medium with aeration and/or agitation, at 25°–30° C., preferably at 27° C., for about 3-7 days. Aeration may be performed by sparging. Agitation may be performed by impellor. About 3 days after the start of the fermentation, accumulation of a considerable amount of pullulan is observed, and the viscosity of the culture mixture increases.

The pullulan concentration and molecular weight in the medium may be determined at certain intervals, and cultivation may be discontinued when the amount of pullulan concentration approaches a concentration greater than 20 g/L and has a molecular weight between 200 kDa and 500 kDa.

Fermentation may be stopped when the pullulan molecular weight is between 200 kDa and 500 kDa and the viscosity of a 10 wt % solution of the pullulan is between 100 cP and 190 cP. Fermentation may be stopped by pasteurization.

The molecular weight of the pullulan produced during fermentation changes over time during the fermentation process. This is due in part to the production of pullulanase by the microorganism. In one embodiment, the molecular weight of the pullulan produced during the process is controlled principally by the pullulanase produced by the microorganism. This eliminates a further step of addition of a material, such as an acid or an elevated temperature, to the bioreactor to reduce the molecular weight of the pullulan.

The microbial cells may be removed from the liquid medium by centrifuging, and the cell-free liquid medium may be decolorized with activated carbon, if desired.

The pullulan may be purified by precipitation in an organic solvent. Preferably, the supernatant following centrifugation is mixed with a hydrophilic organic solvent, such as methanol or ethanol, to precipitate the accumulated pullulan. If desired, the recovered pullulan is dissolved in warm water and again precipitated by solvent.

The pullulan obtained after drying is a whitish powder which very readily dissolves in water to form a viscous solution. The molecular weight of the pullulan obtained varies depending on the culture conditions between 50,000 and 4,500,000 Da. The yield of pullulan also varies from 20 to 75% depending on the culture conditions.

In one embodiment, the resulting pullulan has a relatively high concentration of calcium ($Ca^{2+}$) and magnesium ($Mg^{2+}$) ions. The fermentation media contains calcium phosphate and magnesium chloride. This results in a final pullulan product containing relatively high amounts calcium and magnesium. In addition, the use of a precipitation process, and the absence of an ion exchange process to remove ions, retains a significant fraction of the starting calcium and magnesium. In one embodiment, the pullulan has a $Ca^{2+}$ content of at least 50 mg/kg, or at least 100 mg/kg, or at least 200 mg/kg, or at least 300 mg/kg, or even at least 500 mg/kg. In another embodiment, the pullulan has a $Mg^{2+}$ content of at least 10 mg/kg, or 20 mg/kg, or 30 mg/kg, or at least 40 mg/kg, or even at least 50 mg/kg. In one embodiment, the ratio of $(Mg^{2+}+Ca^{2+})/K^+$ is greater than 3, or greater than 5, or greater than 10, or even greater than 15.

In another embodiment of the invention, a dry fermentation media is provided that is suitable for use for making a fermentation medium for making organic pullulan. In one embodiment, the dry fermentation media comprises
(a) a carbon source in an amount of from 89 wt % to 99 wt %
(b) a nitrogen source in an amount of from 0.9 wt % to 9 wt %; and
(c) a phosphate source consisting of calcium phosphate in an amount of from 0.2 wt % to 0.7 wt %.

In one embodiment, the dry fermentation media comprises magnesium chloride in an amount of from 0.009 wt % to 1.6 wt %.

It should be understood that the embodiments described herein are not limited thereto. Other embodiments of the present disclosure will be apparent to those skilled in the art from consideration of the specification and practice of the disclosed embodiments. The following examples should be considered as exemplary only, with a true scope and spirit of the present disclosure being indicated by the following claims.

Example 1

An organic pullulan fermentation medium was prepared as follows. 2 g/L of monocalcium phosphate ($Ca(H_2PO_4)_2$), 0.2 g/L of magnesium sulfate ($MgSO_4$), and 1 g/L sodium chloride (NaCl) were added to water and allowed to evenly disperse under vigorous agitation for at least 15 minutes. The monocalcium phosphate did not completely dissolve, but evenly dispersed into a suspension. 3 g/L of organic yeast extract was then added to the mixture and allowed to dissolve. Finally, 100 g/L of organic sucrose was added to the mixture and allowed to dissolve. After adjusting to the final volume with additional water, the solution pH was measured at 4.85. The media was steam sterilized at 121 C. for 40 minutes.

An inoculum culture was prepared by inoculating a sterilized 125 mL shake flask containing 30 mL of the organic pullulan fermentation medium with a scraping from a plate culture of *A. pullulans*. The plate culture was grown on potato dextrose agar. Shake flasks were then passaged at a dilution rate of 1:60 at least every 4 days until enough biomass was achieved to obtain 0.32 mg/mL initial biomass concentration in bioreactors.

The bioreactors were pre-filled with sterile organic pullulan fermentation media and controlled to a temperature of 28 C and agitated at a power input of 700 W/m$^3$ with a single Rushton impeller prior to inoculation and for the duration of the fermentation. Inoculum was then added to the reactor at a volume sufficient to yield a reactor biomass concentration of 0.32 mg/mL. Dissolved oxygen was controlled to >50% air saturation by sparging pure oxygen through a 15 μm stone sparger. The reactor gassing system was designed such that an oxygen transfer rate of at least 110 mM/hr was achieved in order to maintain non-hypoxic conditions. The exhaust gas was routed through a condenser in which the condensate was returned directly to the fermentation media. The working volume of the reactors was 1.25 L, and the total reactor volume was 2 L. The fermentation was then allowed to progress for 93 hours. The pH was uncontrolled. The fermentation was halted by heating the culture to >60 C. at 93 hrs.

The culture was sampled daily to measure biomass concentration, pullulan concentration, and pullulan molecular weight.

Biomass concentration was determined as follows. A 30 mL sample was removed from the bioreactor and placed in a pre-weighed 50 mL centrifuge tube. The sample was then centrifuged at a force of 10000 g for 20 minutes. The supernatant was retained to determine pullulan concentration and molecular weight. The pellet was rinsed with 10 mL water, re-suspended, and centrifuged for an additional 20 minutes at a force of 10000 g. The pellet was then flash frozen and lyophilized to dryness. The dried pellet was then weighed and the biomass concentration calculated based on the volume of the bioreactor sample and weight of the pellet.

Pullulan concentration was determined by precipitating 20 mL of the first supernatant from the biomass analysis in 90% cold ethanol at a ratio of 1:1.4. The precipitated pullulan was then dissolved in water at 10 wt %. This solution was then precipitated again in fresh cold ethanol at the same ratio. The resulting pellet was then dried and weighed. The pullulan concentration was then determined based on the volume of supernatant sample and weight of dried pullulan pellet.

The pullulan molecular weight was determined by dissolving the dried pullulan pellet in water to a concentration of 10 mg/mL. The resulting solution was then filtered through a 0.45 um filter and then injected onto a High Pressure Liquid Chromatography (HPLC) system. The HPLC system was outfitted with a size exclusion column. The pullulan polymer was retained on the column for a time directly related to the polymer size and conformation. The retention time was determined by detecting the pullulan elution via a refractive index detector. The polymer size was determined by the response of the polymer in a multi-angle laser light scattering detector. The response in the multi-angle laser light scattering detector was normalized and verified by the measurement of other known molecular weight standards.

Example 2

Figure 2B:
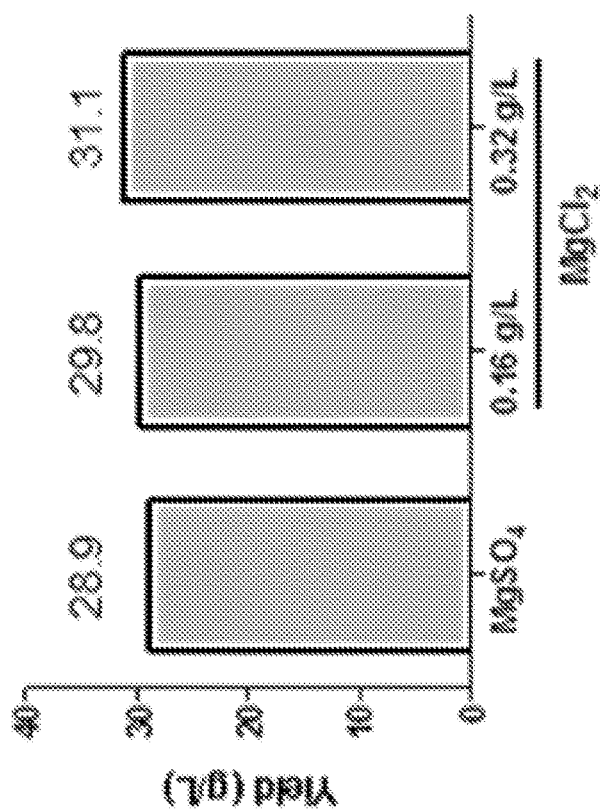
FIG. 2 shows pullulan concentration, molecular weight, and biomass concentration measured in Example 2.
Figure 2A:
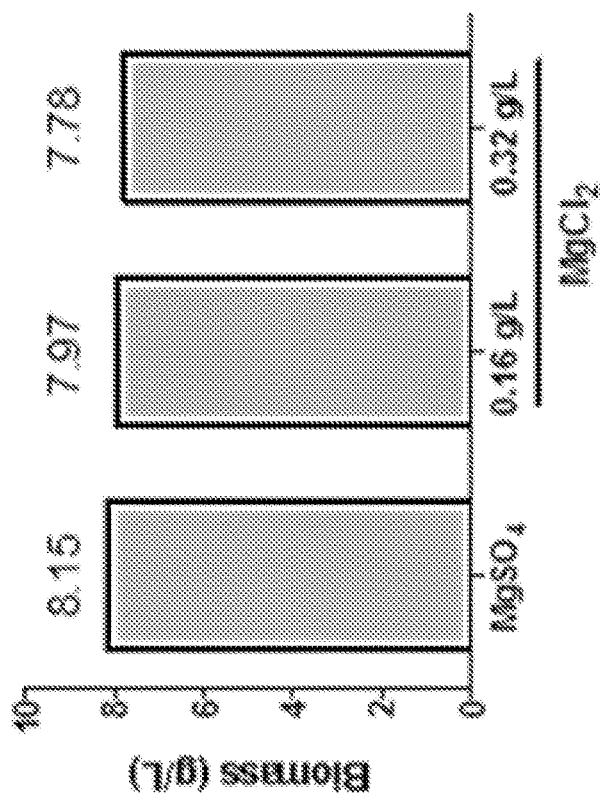

In this Example cell cultures were passaged and maintained as described in Example 1, including the passaging of the inoculation train and the organic pullulan media recipe. In order to evaluate a wholly certified organic pullulan media, we evaluated substituting $MgSO_4$ with a certified organic $MgCl_2$ (Mitoku; Tokyo, Japan). In this experiment, 3 separate 125 mL PETG shake flasks were inoculated with 0.5 mLs of inoculum into a volume of 30 mLs organic pullulan media (1:60). One of these shake flasks contained media with the same composition as described in Example 1. For the other two shake flasks, $MgCl_2$ was substituted for the $MgSO_4$ at concentrations of 0.16 g/L and 0.32 g/L (the rest of the components were the same as outlined in Example 1). These shake flask cultures were grown for 4 days in an orbital shaker incubator at 28° C. at 200 RPM shaking. On the fourth day, these shake flask cultures were analyzed for pullulan yield and biomass using the same procedures as described in Example 1. The results from this study are shown in FIG. 2.

Example 3

In this example, pullulan was produced following the process of Example 2. This pullulan (termed pullulan A) and a representative sample of pullulan produced by Hayashibara (termed pullulan B) was analyzed for Mg2+ and Ca2+ content following the standard protocols SM3111B and D (Flame Atomic Absorption Spectroscopy) respectively. Each pullulan sample was analyzed in triplicate. From this analysis it was determined that the concentration of both Mg2+ and Ca2+ is higher in pullulan A than pullulan B.

TABLE 1

Results of Metal Analysis of Pullulan

| | Pullulan A | | | | Pullulan B | | | |
|---|---|---|---|---|---|---|---|---|
| | $Mg^{2+}$ (mg/kg) | $Ca^{2+}$ (mg/kg) | $K^+$ (mg/kg) | $(Mg^{2+}+Ca^{2+})/K^+$ | $Mg^{2+}$ (mg/kg) | $Ca^{2+}$ (mg/kg) | $K^+$ (mg/kg) | $(Mg^{2+}+Ca^{2+})/K^+$ |
| Replicate 1 | 66.8 | 746 | 48.1 | 16.9 | 2.57 | 20.5 | 11.4 | 2.0 |
| Replicate 2 | 66.0 | 696 | 44.2 | 17.2 | 2.73 | 21.9 | 11.4 | 2.2 |
| Replicate 3 | 66.0 | 688 | 43.6 | 17.3 | 2.52 | 39.7 | 11.1 | 3.8 |
| Mean ± St. Dev | 66.3 ± 0.5 | 710 ± 31.4 | 45.3 ± 2.3 | 17.1 ± 0.2 | 2.6 ± 0.1 | 27.4 ± 10.7 | 11.3 ± 0.2 | 2.6 ± 1.0 |

Values expressed in mg metal per kilogram pullulan

What is claimed is:

1. A process for manufacturing pullulan, comprising:
   a. preparing a fermentation medium comprising water, a nitrogen source, a carbon source, a phosphate source, and a magnesium source;
   b. inoculating said fermentation medium with a pullulan producing microorganism;
   c. culturing said microorganism in said fermentation medium so as to produce pullulan in said fermentation medium;
   wherein said phosphate source comprises calcium phosphate and the pullulan has a ratio of $(Mg^{2+}+Ca^{2+})/K^+$ greater than 5.

2. The process of claim 1 wherein said phosphate source consists of calcium phosphate.

3. The process of claim 1 wherein said fermentation medium has an initial calcium phosphate concentration of from about 0.25 g/L to about 4 g/L.

4. The process of claim 1 wherein said magnesium source is magnesium chloride.

5. The process of claim 1 wherein said fermentation medium has an initial concentration of magnesium chloride of from 0.01 g/L to 1 g/L.

6. The process of claim 1 wherein said nitrogen source is yeast extract, $NH_4OH$, L-glutamine, $NaNO_3$, $NH_4Cl$, L-arginine, or any mixture thereof.

7. The process of claim 1 wherein said nitrogen source is yeast extract.

8. The process of claim 1 wherein said carbon source is glucose, maltose, lactose, sucrose, fruit and vegetable syrups, fruit and vegetable molasses, or a mixture thereof.

9. The process of claim 1 wherein said carbon source is sucrose.

10. The process of claim 1 wherein said microorganism is Aureobasidium pullulans.

11. The process of claim 1 wherein said microorganism is Aureobasidium pullulans ATCC No. 42023.

12. The process of claim 1 wherein said culturing of said microorganism is stopped by pasteurization.

13. The process of claim 1 wherein the molecular weight of said pullulan is reduced by pullulanase produced by said microorganism, and said process is free from a step of adding an acid or heat to reduce the molecular weight of said pullulan.

14. The process of claim 1 wherein said fermentation medium has an initial pH of from 2.5 to 8.

15. The process of claim 1 wherein said microorganism is cultured for at least 3 days.

16. Pullulan produced by:
   preparing a fermentation medium comprising water, a nitrogen source, a carbon source, a phosphate source comprising calcium phosphate, and a magnesium source;
   inoculating the fermentation medium with a pullulan producing microorganism; and
   culturing the microorganism in the fermentation medium to produce the pullulan, the pullulan having a ratio of $(Mg^{2+}+Ca^{2+})/K^+$ greater than 5.

17. The pullulan of claim 16 having a molecular weight of from 200 to 500 kDa.

18. Pullulan having a $Ca^{2+}$ content of at least 50 mg/kg and a ratio of $(Mg^{2+}+Ca^{2+})/K^+$ greater than 5.

19. Pullulan having a $Mg^{2+}$ content of at least 10 mg/kg and a ratio of $(Mg^{2+}+Ca^{2+})/K^+$ greater than 5.

20. A capsule comprising the pullulan of claim 19.

* * * * *